United States Patent [19]
Salort

[11] Patent Number: 5,020,521
[45] Date of Patent: * Jun. 4, 1991

[54] EXTERNAL APPARATUS FOR MOTOR HANDICAPS OF AT LEAST ONE UPPER LIMB

[76] Inventor: Guy J. Salort, 219, rue Raymond Losserand, 75014 Paris, France

[ * ] Notice: The portion of the term of this patent subsequent to Dec. 24, 2002 has been disclaimed.

[21] Appl. No.: 524,699

[22] Filed: May 17, 1990

Related U.S. Application Data

[60] Continuation of Ser. No. 320,827, Dec. 29, 1988, abandoned, which is a continuation of Ser. No. 774,481, Sep. 10, 1985, abandoned, which is a division of Ser. No. 556,122, Nov. 29, 1983, Pat. No. 4,559,932.

[30] Foreign Application Priority Data

Nov. 10, 1982 [FR] France ................................ 82 18902

[51] Int. Cl.$^5$ ............................ A61F 5/10; A61F 5/04
[52] U.S. Cl. ........................................ 128/77; 128/88
[58] Field of Search ................... 128/73, 83, 87 R, 88, 128/77

[56] References Cited
U.S. PATENT DOCUMENTS

| | | | |
|---|---|---|---|
| 158,893 | 1/1875 | Bissell | 128/88 |
| 4,370,977 | 2/1983 | Mauldin et al. | 128/88 X |
| 4,559,932 | 12/1985 | Salort | 128/77 |

FOREIGN PATENT DOCUMENTS 22535604  5/1984  France ................................ 128/77

Primary Examiner—Edgar S. Burr
Assistant Examiner—Kimberly L. Asher
Attorney, Agent, or Firm—Cushman, Darby & Cushman

[57] ABSTRACT

An external orthesis for motor handicaps of the hand of an upper limb of a human, comprising a para-skeleton for the upper limb and hand. The construction of the orthesis is such that the physiological joints are held under compression and the weight of the handicapped hand is dynamically neutralized. The orthesis is adapted to be operated by operation of the scapular motor to cause manipulation of the various physiological joints. Use of the orthesis speeds recovery of sensitivity and mobility.

8 Claims, 4 Drawing Sheets

EXTERNAL APPARATUS FOR MOTOR HANDICAPS OF AT LEAST ONE UPPER LIMB

This is a continuation of application Ser. No. 07/320,827, filed on Dec. 29, 1988, which was abandoned upon the filing hereof, continuation of Ser. No. 06/774,481, which is a division of Ser. No. 06/556,122, now abandoned.

FIELD OF THE INVENTION

The present invention relates to an external apparatus for motor handicaps of at least one upper limb. This apparatus allows the subject to use his handicapped limb by using exclusively the energy coming from the scapular motor.

BACKGROUND OF THE INVENTION

Until now, in the state of the art, three types of ortheses have been proposed for the upper limb: in the first type the various parts of the limb are tightly held in shells which are actuated with respect to each other by means of motor devices controlled by the subject, such as, for instance, an electric motor or an artificial inflatable muscle; in the second type, the limb is supported in a given position by means of a rigid frame; in the third type, the limb is supported by an external rigid structure articulated at several points by pins so as to allow a given mobility of the various parts of the limb with respect to each other but the subject can only control the movements of his limb by an external action, either with an external motor or by an action of his other limb. In all these cases, the limb is entirely supported and the movement of the joints when it does exist, is far more limited than the physiological movement of the joints.

On the contrary, according to the invention, the limb may have all the normal physiological movements, the joints being capable of operating in all the admissible physiological directions and the control of the limb is effected by the subject himself, without the help of an external motor, by operating the scapular motor constituted by the structure of the shoulder. Depending on whether, by the movements of his shoulder, the subject opens or closes the scapular cone constituted at the level of the connection of the shoulderblade and the clavicle, he produces an action on the humerus which, by means of the apparatus according to the invention, results in a set of actions on all the parts of the limb which cause the joints to operate within the constraints of the normal physiological movement.

OBJECTS OF THE INVENTION

The object of the present invention is to provide an autonomous orthesis which ensures that the limb joints are placed in compression by means neutralising the weight of the limb in a dynamic manner. One thus allows the motor units to be informed and reactivated by a modulation of the falling of the handicapped limb with respect to time and space; one thus improves and accelerates the overall recovery of the voluntary gripping movement.

BRIEF DESCRIPTION OF THE INVENTION

The invention therefore provides an external apparatus for motor handicap of at least one upper limb, the said apparatus allowing the subject to move his handicapped limb, characterised in that it comprises, for each handicapped limb, a) on the one hand, a thoraco-scapular structure constituted by two sub-assemblies:
  firstly, a shoulder brace formed by at least three semi-rigid shells which are interconnected in a flexible manner, the first being disposed over the upper angle of the pectoral muscle and passing over the upper edge of the trapezius, the second being disposed over the clavico-trapezoidal zone at the top of the shoulder, the third being disposed opposite the scapula, there being at least one elastic tensioner between the second shell and each one of the two others;
  secondly, an attachment sub-assembly disposed around the torso and connected to the above mentioned shoulder brace at at least three fastening points distributed over either side of the shoulder;
b) on the other hand, a para-skeleton for the upper limb and the hand comprising;
  firstly, five elements to connect with the limb and disposed respectively at the level of the upper and lower humeral parts, of the upper and lower cubitoradial parts and of the hand, the upper humeral connection element comprising the second shell of the shoulder brace and a peripheral strap surrounding the limb, each one of the other four connector elements comprising a semi-rigid shell made in one, or several pieces and at least one peripheral strap surrounding the limb;
  secondly elastic means disposed between the two above mentioned connection elements comprising:
  a first spring lever operating in flexion and torsion, fixed between the second shell of the shoulder brace and the shell of the lower humeral connection element, substantially parallel to the humerus along the external edge of the limb,
  a second spring lever analogous to the first, fixed between the shell of the upper cubito-radial connection element and the shell for the hand, substantially parallel to the cubitus along the internal edge of the limb.
  two elastic tensioners disposed on the external and internal edges of the arm, between the lower humeral and upper cubito-radial connection elements, and
  two elastic tensioners disposed between the lower cubito-radial connection element and the connection element for the hand.

In a preferred mode of embodiment, the attachment sub-assembly is connected to the shoulder brace at three attachment points, the first situated in the anterior zone of the first shell of the shoulder brace, the second situated in the lower zone of the third shell, and the third situated in the upper internal zone of the third shell; advantageously, the attachment sub-assembly is constituted by:
  a belt passing around the subject at waist level, the said belt may assume larger or narrower widths and may constitute a corset, the said belt being single if the subject is handicapped in both upper limbs and carries an apparatus for each one of the two limbs;
  an anterior linkage constituted by a thoracic transmission element and an elastic connector, the said transmission element having an end fixed on the belt at the level of the iliac spine on the side opposite the equipped limb and having its other end connected by the above mentioned elastic connector to the first shell of the shoulder brace;

a first lateral elastic linkage held between the belt at the level of the iliac spine on the side of the equipped limb and the third shell of the shoulder brace;

a second lateral elastic linkage held on the side opposite the equipped limb, between the third shell of the shoulder brace and the above mentioned anterior linkage.

According to a preferred embodiment, the thoracic transmission element is a spring lever which forms an angle of approximately 30° with the axis of the subject's body; the first lateral elastic linkage is connected to the third shell of the shoulder brace opposite the base of the shoulder blade and the second elastic lateral linkage is connected to the third shell of the shoulder brace, near the inner part of the shoulder blade spine.

Provision may advantageously be made for the second shell of the shoulder brace to be connected to the third shell of the said shoulder brace by a tensioner fixed between the upper posterior zone of the second shell and the central zone of the third shell, a deflector guide constraining the tensioner to pass opposite the external part of the shoulder blade spine; similarly, provision may be made for the second shell of the shoulder brace to be connected to the first shell by a tensioner fixed between the upper anterior zone of the second shell and the internal posterior zone of the first shell, a deflector guide constraining the tensioner to remain opposite the clavicular zone over approximately half of its length. These deflector guides for the tensioners may be constituted by pulleys.

The spring levers of the apparatus according to the invention generally work in flexion and in torsion. They are advantageously constituted by flexible metal blades made, in particular, of steel with pronounced elastic characteristics.

In a preferred mode of embodiment, the element for the lower humeral connection and the element of the upper cubito-radial connection each comprise a single shell, the two shells having their adjacent edges separated by an articular gap having a substantially constant width comprised between approximately 5 and 15 mm and being connected opposite this gap by elastic means disposed on either side of the olecranon, the edge of the lower humeral shell along the said gap having a convex shape opposite the epicondyle and the epitrochlearis and a concave shape opposite the olecranon, the edge of the upper cubito-radial shell having a complementary shape; the lower or upper humeral connection element covers, advantageously, approximately the lower third of the upper arm; the shell of the lower cubito-radial connection element is constituted by two half shells covering respectively the radial and cubital parts of the limb, these two half shells being separated by a groove opposite the cubitus, the limb being introduced into the shell on the side opposite the groove, the two half shells being tightened around the limb by two peripheral straps disposed at the upper and lower ends of the said shell; the element of the lower or upper radial connection covers approximately on third of the fore-arm.

In a preferred embodiment, the connection element for the hand comprises:firstly, a shell constituted by three segments, the first segment covering the thenar eminence, the second segment covering the second, third and fourth carpal and metacarpal bones as far as the base of the fingers, the third segment covering the hypothenar eminence;and secondly,(a) a first peripheral strap disposed over the above mentioned first and second segments and surrounding the hand, with the exception of the thumb at the level of the lower part of the metacarpal bones and (b) a second peripheral strap surrounding the carpus and passing over the three segments near the wrist, the said second peripheral strap being connected to the lower cubito-radial connection element by a rubber strap; the connection element for the hand is connected to the lower cubito-radial connection element by two tensioners, the one between the base of the thumb and the lower radial zone and the other between the lower cubital zone and the central palmar zone of the metacarpus passing diagonally above the hand; the second spring lever of the apparatus is disposed opposite the gap between the cubitus and the inner edge of the forearm and it has its lower end fixed on the third segment of the shell of the connection element for the hand, somewhat ahead of the pisiform bone.

In a first variant of the embodiment of the connection element for the hand a strap carried by the first segment of the shell of the hand surrounds the base of the thumb, the other fingers of the hand not being fitted with the apparatus. In a second variant, each finger of the hand is fitted with an elastic crossed tensioner disposed between a supporting end fitting placed above the metacarpus and a supporting end fitting placed above the second phalanx; the supporting end fitting placed at the level of the metacarpus is carried by the segment of the shell of the hand which corresponds to it and the supporting end fitting placed at the level of the second phalanx is carried by a finger stall which surrounds the end of the finger, each supporting end fitting comprises preferably an adjustable angular orientation element capable of turning around an axis substantially perpendicular to the bone which it surmounts.

DESCRIPTION OF THE DRAWINGS

To render the object of the invention more readily understood, there will now be described, by way of a purely illustrative and non-restrictive example, a mode of embodiment represented in the attached drawings.

In these drawings.

DESCRIPTION OF THE PREFERRED EMBODIMENT

Figure 1:
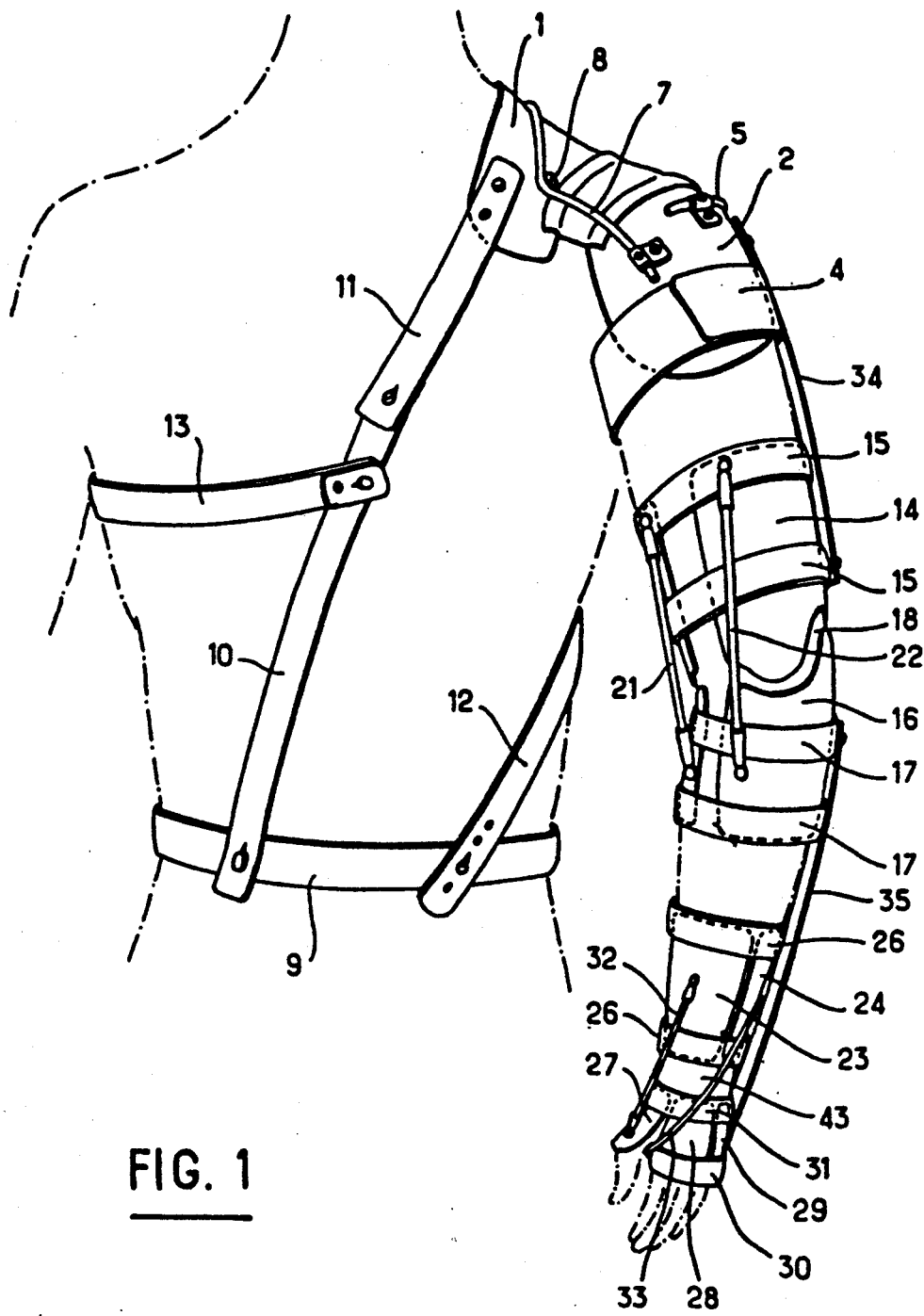
FIG. 1 shows a schematic front view of an apparatus according to the invention carried by a subject with a motor handicap of the left arm.

Referring to the drawings, it will be seen that the apparatus shown comprises a thoraco-scapular structure constituted by a shoulder brace and a fastening sub-assembly.

Figure 2:
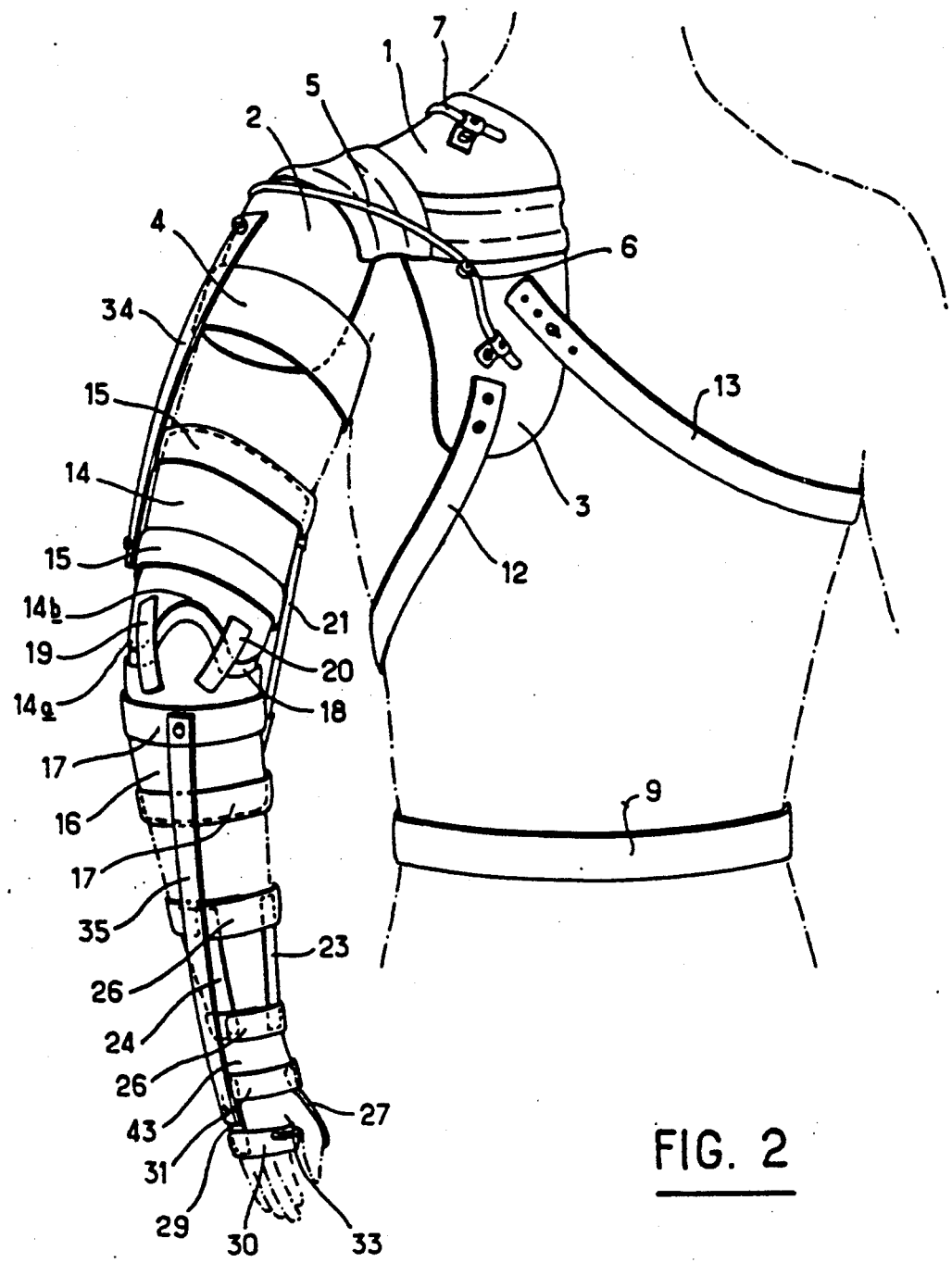
FIG. 2 shows a schematic posterior view of the apparatus of FIG. 1.

The shoulder brace is formed by two semi-rigid shells made of a moulded plastic material. The first shell 1 is disposed over the upper angle of the pectoral muscle and passes over the upper edge of the trapezius. The second shell 2 is disposed over the claviculo-trapezoidal zone at the tip of the shoulder. The third shell 3 is disposed opposite the scapula, that is to say, on the shoulder blade (FIG. 2). These three shells, 1,2,3 are interconnected by rubber bands, but they are separated from each other by sufficient space to allow relative motion between them. The shape of these shells is anatomically adapted to the particular subject who is to wear them.

Shell 2 of the shoulder brace is joined to a peripheral strap 4 which is intended to surround elastically the upper part of the arm, the grip being ensured by a releasable fastening known under the commercial designation of "VELCRO" for instance. Shell 2, is moreover, connected to shell 3 by a tensioner 5 attached to shell 2 at a point of the postero-upper zone of this shell and to shell 3 opposite the sub-spinal part of the shoulder blade, substantially in the central zone of the shoulder blade. Tensioner 5 passes over a pulley 6 carried by shell 3 at a point situated at the level of the spine of the shoulder blade, substantially at a distance of one third, starting from the outside.

Shell 2 is also connected to shell 1 by a tensioner 7 attached to shell 2 at a point of the upper part of this shell which is at the level of the cradle of the biceps. Tensioner 7 is attached to shell 1 at a point situated opposite the inner sub-spinal portion of the shoulder blade in the zone of the insertion of the trapzius. Tensioner 7 passes over a pulley 8 carried by shell 1 and disposed opposite the coracoid.

The rubber band connecting shells 1 and 2 is disposed towards the front of the central deltoid muscle towards the clavicle. The rubber band ensuring the linkage between shell 2 and shell 3 is disposed towards the back of the central deltoid muscle towards the spine of the shoulder blade. The shapes of shells 1, 2, 3 and the linkages fitted provide a displacement angle for the arm in relation to the shoulder of approximately 45° towards the front or towards the back. The rubber band ensuring the linkage between shells 1 and 3 is disposed substantially above the spine of the shoulder blade.

The second sub-assembly of the thoraco-scapular structure is the attachment sub-assembly. This sub-assembly comprises a belt 9 passing round the subject at waist level. To this belt, there is joined an anterior linkage constituted by a thoracic spring lever 10 and an elastic connector 11. The thoracic spring lever 10 is attached to belt 9 at the level of the iliac spine at the opposite side from the limb fitted with the apparatus; it is connected to the elastic connector 11 at the level of the xiphoid process, that is to say, at the tip of the sternum. The elastic connector 11 is attached to shell 1 of the shoulder brace at a point situated on the lower anterior part of shell 1 below the clavicle. The elastic connector 11 is constituted by an elastic band; the thoracic spring lever 10 is constituted by a metal steel blade of the type "XC75", the blade having a thickness of 0.5 mm and a width of 25 mm; the length of the blade depends on the subject's anatomy. It would be possible to consider replacing this spring lever 10 by a thoracic transmission element which would be solely constituted by a strap, but the result seems less satisfactory in this case as regards the transmission of the energy from the scapular motor to the handicapped limb.

Belt 9 is connected by a first lateral elastic linkage 12 with shell 3 of the shoulder brace. The lateral elastic linkage is constituted by an elastic strap; it is attached to belt 9 at the level of the iliac spine on the side of the equipped limb; it is attached to shell 3 at the level of the tip of the shoulder blade.

Between the junction zone of spring lever 10 with the elastic connector 11 on the one hand, and shell 3 on the other, there is a second lateral linkage 13 constituted by an elastic band. The point of attachment of band 13 on shell 3 is disposed in the upper internal zone of shell 3 slightly below the inner end of the shoulder blade spine. The positioning of band 13 is such that the mamilla of the side opposite to the equipped limb remains free.

The apparatus according to the invention associates the thoraco-scapular structure described above with a para-skeleton for the upper limb and the hand. This para-skeleton comprises five linkage elements with the handicapped limb. The upper humeral linkage element is constituted by shell 2 and the peripheral strap 4; it extends substantially over one third of the length of the upper arm. The lower humeral linkage element is constituted by a shell 14 which has, on the inner side of the arm, an opening allowing this limb to be introduced. Shell 14 is kept in position on the limb by means of a peripheral strap 15 and the combination 14, 15 covers the lower humeral part of the upper arm over approximately one third of the length of the upper arm. The peripheral strap 15 is constituted by two bands, each analogous to band 4, disposed at the upper and lower ends of shell 14.

The linkage element for the upper cubito-radial parts also comprises a shell 16 analogous to shell 14. Shell 16 is also open on the side of the inner part of the forearm; it is fixed on the forearm by a peripheral strap 17, constituted by two elastic bands each analogous to band 4, the two bands being placed at the upper and lower ends of shell 16. Shells 14 and 16 are separated at the level of the elbow by a gap 18 which has a substantially constant width and equal to 8 mm. To permit the articulation of the forearm in relation to the upper arm, the lower edge of shell 14 has two rounded convex shapes 14a opposite the epicondyle and the epitrochlearis, these two convex shapes being separated by a rounded concavity 14b opposite the olecranon. The upper edge of shell 16 has a complementary shape so that the articular gap 18 remains at a substantially constant width. This cut out allows a relative movement of shell 16 in relation to shell 14 which corresponds to the elbow joint. Shells 14 and 16 are linked by two tensioners 19 and 20 disposed on either side of the olecranon above the articular gap 18. Moreover, shells 14 and 16 are interconnected by two elastic tensioners 21 and 22, disposed respectively in the hollow of the elbow on the inner and outer edges of the limb.

The lower cubito-radial linkage element comprises a shell constituted by two half shells 23, 24 covering respectively the radial part and the cubital part of the forearm. These two half shells are separated by a groove 25 and they are held tight around the limb by two peripheral straps 26 disposed at two upper and lower ends of the said shell 23, 24. The lower cubito-radial linkage element extends over substantially the lower third of the forearm. The limb is introduced between the two half shells 23, 24 on the opposite side to groove 25.

The linkage element for the hand comprises a shell constituted by three segments 27, 28, 29. Segment 27 covers the thenar eminence. Segment 28 covers the second, third and fourth carpal and metacarpal bones as far as the base of the fingers. The third segment 29 covers the hypothenar eminence. These three segments are kept in position on the calix of the hand by means of two peripheral straps. A first peripheral strap 30 is disposed over the segments 28 and 29 at the level of the metacarpal bones and it surrounds the hand wit the exception of the thumb. A second peripheral strap 31 surrounds the carpus and passes over the three segments 27, 28, 29 near the wrist. The peripheral straps 30 and 31 have a width of approximately 2 cm. The first peripheral strap 30 is connected elastically to the lower cubital zone of half shell 24 by an elastic tensioner which passes diagonally over the carpus and metacarpus and is fixed in the palmar portion of strap 30 substantially opposite the base of the second finger. An elastic tensioner is disposed between the lower radial zone of half shell 23 and segment 27 at the level of the base of the thumb. The linkage element for the hand is connected to the lower cubito-radial linkage element by a rubber band disposed over the wrist.

All the shells 14, 16, 23, 24, 27, 28, 29 of the para-skeleton are made of a moulded plastic material conforming to the anatomy of the subject. All the peripheral straps 15, 17, 26, 30, 31 are analogous to strap 4.

Figure 4:
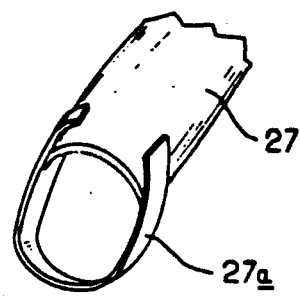
FIG. 4 shows, in perspective, a first variant of the shell of the hand wherein the first segment is fitted with a strap to support the thumb.

In the first variant represented in FIG. 4, segment 27 is fitted with a strap 27a forming a loop and surrounding the base of the column of the thumb. This strap 27a may be constituted by an elastic band inserted at the lower end of segment 27. The other fingers are not equipped.

Figure 5:
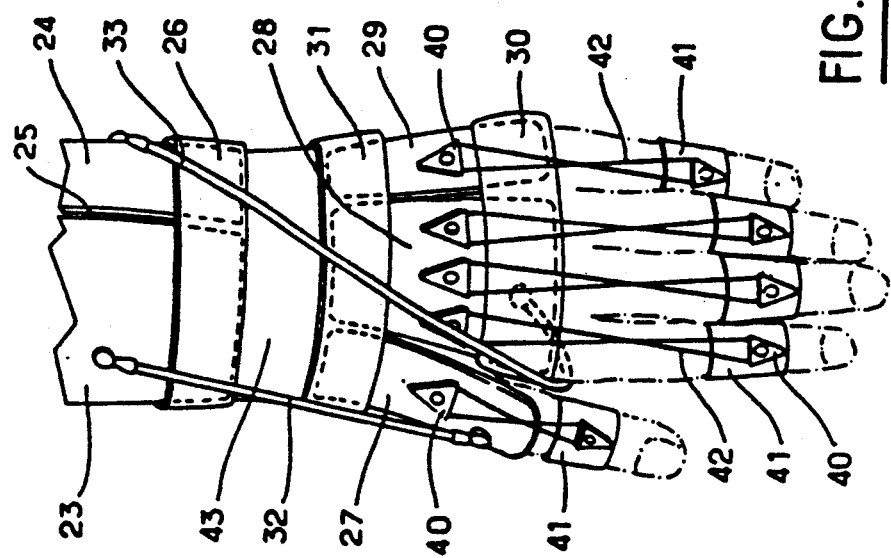
FIG. 5 shows, in plan, a second variant of the embodiment of the linkage element for the hand wherein each finger is fitted with a crossed tensioner.
Figure 3:
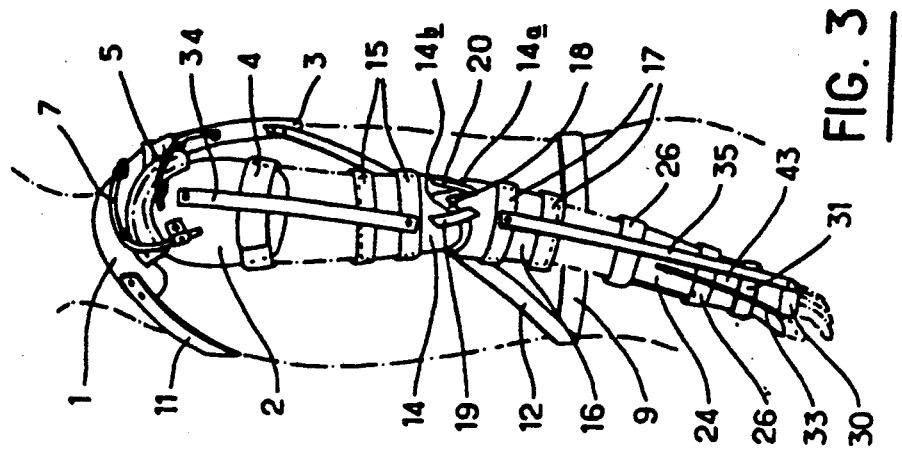
FIG. 3 shows an external side view of the apparatus of FIGS. 1 and 2.
Figure 6:
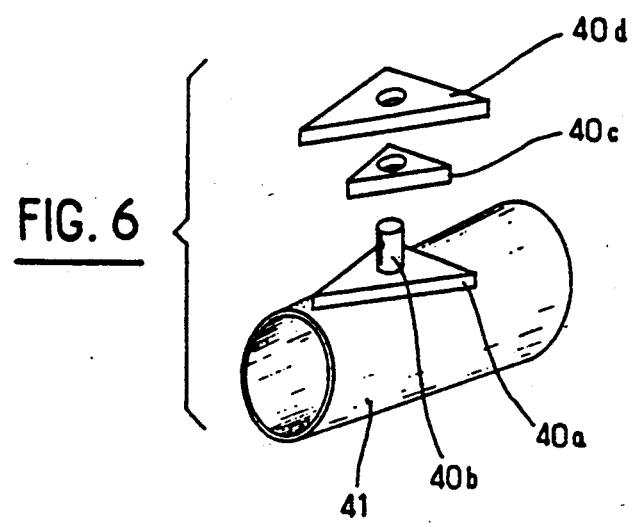
FIG. 6 shows schematically in an exploded perspective, the embodiment of a supporting end fitting for the crossed tensioners of FIG. 5.

In a second variant represented in FIGS. 5 and 6, each one of the fingers of the hand is equipped. In this case, each one of segments 27, 28, 29 carries, opposite each one of the metacarpal bones, a supporting end fitting designated by 40 as a whole. Segment 27 thus carries one end fitting 40; segment 28 carries three end fittings 40; and segment 29 carries one end fitting 40. All the end fittings 40 are identical. Each end fitting 40 is constituted by a base 40a of triangular shape supporting a cylindrical pin 40b substantially perpendicular to the bone which it surmounts. On base 40a, there rests a triangular guide plate 40c which is fitted on pin 40b and which is kept in position against base 40a by a triangular cover 40d of the same shape and same dimensions as base 40a, cover 40d also being fixed on pin 40b. The stack 40a 40c, 40d, is kept together tightly for example, by catch engagement of lid 40d on the tip of pin 40b. The position of guide plate 40c between base 40a and cover 40d is adjustable by rotation around pin 40b but because of the tight grip of the stack, this position is maintained after adjustment by the friction of guide plate 40c between base 40a and cover 40d. The facing surfaces may be granulated or striated to ensure satisfactory friction.

Each one of the fingers of the hand is fitted at the level of the second phalanx with a finger stall 41 having a slightly frustoconical shape. Each finger stall comprises an end fitting 40 identical with the one which has been previously described. All the end fittings 40 are disposed on the back of the hand. For each of the fingers of the hand, an elastic tensioner 42 is placed in position between the supporting end fitting 40 situated at the level of the second plalanx and the end fitting 40 situated at the level of the metacarpus. Tensioner 42 is crossed X wise and passes around guide plate 40c of each of end fittings 40 associated therewith. In this way, by suitably orientating the guide plate 40c of each one of the two supporting end fittings, one may regulate the direction of the compressive stress applied to the finger joints. Tensioners 42 constitute elastic brakes for the closing of the hand.

The para-skeleton described above comprises, moreover, in a way that is essential for the functioning of the apparatus according to the invention, two spring levers constituted by metal blades analogous to the spring levers 10. The first spring lever 34 is fixed between a point of the central zone of shell 2 of the shoulder blade and shell 14; it is substantially parallel to the humerus along the outer edge of the arm. The second spring lever 35 is fixed between shell 16 and segment 29; it is substantially parallel to the cubitus opposite the space comprised between the cubitus and the inner edge of the forearm. Its fastening on segment 29 is effected somewhat ahead of the pisiform.

It will be seen that the apparatus described above allows a person with a motor handicap of the upper limbs to recover a certain mobility of his handicapped limb.

In effect, the tensions of the various tensioners of the spring levers of the apparatus are adjusted so that in a rest position, the forearm should form an angle of approximately 30° with the upper arm and that the wrist should be in slight dorsal flexion (approximately 10° in an upward direction); moreover, the fingers are in slight palmar flexion, (approximately 15° downward) and the thumb is in an abducted position so as to open the prehensile grip.

When the subject moves his shoulder backwards he opens the scapular cone constituted by the shoulder blade and the clavicle which produces the rising of the humerus. In this movement, the lever arm of the action of the weight of the forearm in relation to the elbow joint increases and there results therefrom a slight extension by the opening of the elbow angle, the tensioners 21, 22 restraining this opening. Under the effect of the weight, the hand has a tendency to move downwards which is checked by tensioners 32, 33. The hand has a tendency towards closing which is checked by tensioners 42.

If the subject raises his shoulder upwards and towards the front, a return movement is effected with respect to the previous movement. The humerus is drawn back; the lever arm of the weight of the forearm in relation to the elbow decreases and under the action of tensioners 21, 22 the forearm rises again which slightly closes the elbow angle. The hand turns slightly, tending to have the palm upwards and the fingers open.

It will be seen, therefore, that the scapular motor allows, by combining all the possible movements of the shoulder, the control of the apparatus according to the invention. The movements of the humerus, when the subject displaces his shoulder, are not only controlled by the physiological joints but also by the spring lever 34 which, being fixed to shell 2 of the shoulder brace, sustains tensile stresses applied to the shoulder brace by the attachment means 9, 10, 11 12, 13. The movement is transmitted from the arm to the hand by spring lever 35, thus the weight of the handicapped limb is neutralised dynamically.

It has been found that the working of the limb equipped in this way allows the motor unit to be reactivated which accelerates the recovery of the gripping movement. Moreover, the subject who uses such an apparatus and makes use of his handicapped limb recovers a large part of the sensitivity of the limb in a spectacular way.

It shall be duly understood that the mode of embodiment described above is in no way restricted and may give rise to any desirable modifications without thereby departing from the scope of the invention.

I claim:

1. An external apparatus for overcoming motor handicaps of at least one hand of a human subject to allow the subject to move his hand comprising, (a) a lower radial-cubital connecting assembly comprised of two part-shells respectively covering the radial part and the cubital part of the forearm, said part shells being separated by a narrow space along the cubitus, and the two part shells being secured around the forearm by at least one peripheral strap so that the forearm can be introduced between the part shells from the side opposite the narrow space, (b) a hand connecting assembly comprising a shell comprised of three segments, a first segment covering the thenar eminence, a second segment covering the second, third, and fourth carpal and metacarpal bones to the base of the fingers, and a third segment covering the hypothenar eminence, a first peripheral strap on the first and second segments and extending generally around the palm of the hand, but not the thumb, in the region of the metacarpals, a second peripheral strap extending around the the wrist and passing over the three segments of the shell in the region of the wrist, said second strap being connected to the lower radial-cubital connecting assembly by elastic means.

2. Apparatus according to claim 1 wherein, the lower radial-cubital connecting assembly is secured around the forearm by two peripheral straps respectively at the upper and lower ends of the two part-shells.

3. Apparatus according to claim 2 wherein, the lower radial-cubital connecting assembly covers about one-third of the forearm.

4. Apparatus according to claim 1 wherein, the hand connecting assembly is connected to the lower radial-cubital connecting assembly by two tensioners, one between the thumb and the lower radial region, and the other between the lower cubital region and the palm and passing diagonally over the back of the hand.

5. Apparatus according to claim 1 wherein, the first segment of the shell of the hand connecting assembly has a strap which extends across the base of the thumb.

6. Apparatus according to claim 1 wherein, the hand connecting assembly comprises a plurality of upper support fittings above the metacarpals, and a plurality of lower support fittings on the fingers at the level of the phalanx, and each finger of the hand is connected to a different upper support fitting by a tensioner band.

7. Apparatus according to claim 6 wherein, the upper support fittings are mounted on the shell segments of the hand assembly, and the lower support fittings are mounted respectively on finger stalls disposed on and surrounding the respective fingers, and each tensioner extends generally longitudinally of the the hand and fingers.

8. Apparatus according to claim 6 wherein, each support fitting comprises a triangular support element mounted for angular orientation about an axis essentially perpendicular to the bone on which it is surmounted.

* * * * *